(12) United States Patent
Ramakrishna et al.

(10) Patent No.: US 11,525,112 B2
(45) Date of Patent: Dec. 13, 2022

(54) FAILURE RECOVERY IN CELL CULTURE BIOREACTORS

(71) Applicant: Global Life Sciences Solutions USA LLC, Marlborough, MA (US)

(72) Inventors: Manoj Ramakrishna, Karnataka (IN); Anoop Bhargav, Karnataka (IN); Umesh Pai, Karnataka (IN)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 266 days.

(21) Appl. No.: 16/474,316

(22) PCT Filed: Dec. 22, 2017

(86) PCT No.: PCT/EP2017/084483
§ 371 (c)(1),
(2) Date: Jun. 27, 2019

(87) PCT Pub. No.: WO2018/122194
PCT Pub. Date: Jul. 5, 2018

(65) Prior Publication Data
US 2019/0338231 A1  Nov. 7, 2019

(30) Foreign Application Priority Data
Dec. 29, 2016 (IN) .............................. 201611044875

(51) Int. Cl.
*C12M 1/00* (2006.01)
*C12M 3/06* (2006.01)
*C12M 1/36* (2006.01)

(52) U.S. Cl.
CPC ............ *C12M 23/58* (2013.01); *C12M 23/14* (2013.01); *C12M 27/16* (2013.01); *C12M 41/48* (2013.01)

(58) Field of Classification Search
CPC ...... C12M 23/58; C12M 23/14; C12M 27/16; C12M 41/48
See application file for complete search history.

(56) References Cited

U.S. PATENT DOCUMENTS

2005/0112542 A1* 5/2005 West .................... G05B 19/042
                                                         435/3
2011/0136225 A1   6/2011 Vunjak-Novakovic et al.
2018/0251722 A1*  9/2018 Patil ....................... C12M 41/48

FOREIGN PATENT DOCUMENTS

JP     2004341645 A    12/2004
WO    2011/005773 A2    1/2011
(Continued)

OTHER PUBLICATIONS

PCT International Search Report and Written Opinion for PCT Application No. PCT/EP2017/084483 dated Apr. 13, 2018 (8 pages).
(Continued)

*Primary Examiner* — William H. Beisner
*Assistant Examiner* — Danielle B Henkel
(74) *Attorney, Agent, or Firm* — Eversheds Sutherland (US) LLP

(57) ABSTRACT

Disclosed is a cell culture system comprising a first cell culture bioreactor system (10) for culturing cells to a predetermined cell density or quantity, the system including a bioreactor volume (20), a process controller (30), process control devices (32) which provide inputs (16) for the culture volume and culture parameter measurement devices (14), wherein the process controller is operable according to plural control program steps to control the process devices to provide inputs for a suitable cell culture environment in the bioreactor volume, and is further operable according to control program steps modified by feedback values from the culture parameter measurement devices, and comprises a memory (36) operable to record data indicative of the
(Continued)

Scenario 3 - One master controller collecting all information progress of the control program steps. Failure of the system can be rectified by moving the bioreactor volume to another similar system which has access to data indicative of any incomplete program steps which steps may have been modified by feedback from the measurement devices.

12 Claims, 4 Drawing Sheets

(56) References Cited

FOREIGN PATENT DOCUMENTS

| WO | 2015/048725 A1 | 4/2015 |
| WO | 2016/062833 A1 | 4/2016 |

OTHER PUBLICATIONS

CN Office Action for Application No. 201780081815.9 dated Jul. 21, 2022, for corresponding U.S. Appl. No. 16/474,316; 23 pages with translation.

* cited by examiner

Scenario 1 - private cloud

Scenario 2 - Instruments talking directly between themselves

Scenario 3 - One master controller collecting all information

FAILURE RECOVERY IN CELL CULTURE BIOREACTORS

CROSS REFERENCE TO RELATED APPLICATIONS

This application claims the priority benefit of PCT/EP2017/084483 filed on Dec. 22, 2017 which claims priority benefit of Indian Application No. 201611044875 filed on Dec. 29, 2016. The entire contents of which are hereby incorporated by reference herein.

TECHNICAL FIELD

The present invention relates to failure recovery methodology in cell culture bioreactor systems.

BACKGROUND

Cell culture bioreactor systems are known which comprise hardware including a bioreactor which provides a generally closed volume, and further hardware and software to measure and control certain environmental parameters so they are maintained within a predetermined range, to provide a consistent environment for the successful multiplication of cells within the volume. To reduce operating costs, it is known to provide a disposable bioreactor, for example in the form of a flexible bag (often called a cell bag) including fluid connectors, and to have the remainder of the hardware as reusable components. In this way, little sterilisation is required between cell culture batches. Whilst such bioreactor systems are robust, failure, is not impossible. For example, the bringing together of, mechanical, electrical power, electronic, software, liquid, and gas functions can lead to numerous potential failure modes.

In addition, for some cell culture procedures, small batches of cells are cultured for specific therapies, for example autologous immunotherapy, where a patient's cells are isolated, manipulated if necessary, expanded and reintroduced into the patient. These batches are usually expanded in process liquid quantities up to 5 liters and more usually in liquids up to 2.5 liters. In those cases, the cell culture regime also includes initiation of the cells into a bioreactor, followed by equilibration, inoculation and then expansion. These initial phases add to the complexity of cell expansion, and require careful process control. The process control is even more important with small cell batch culture because small batches are affected by even very small deviations in the maintained parameters, and, because the cells start the culture process in liquid quantities of around 500 mLiters or less, then deviation in the parameters can quickly take place during a hardware or software failure.

Larger scale process control systems, like those used in a large scale (e.g. 1000 liter) bioreactor control systems, typically include one or more process control devices in communication with one or more process controllers via analog, digital or combined analog/digital buses. The process controller is, in turn in communication with at least one host or operator workstation via suitable input/output (I/O) devices. The process control devices, which may be, for example, pumps, agitators, mass flow controllers, and transmitters, as well as parameter measurement devices such as temperature, pressure and flow rate sensors, perform functions within the process such as increasing or decreasing fluid flow and measuring process parameters. The process controllers receive signals indicative of process measurements made by the process control measurement devices and/or other information pertaining to the process control devices, use this information to implement a control routine, and then generate control signals that are sent over the buses or other communication lines to the process control devices to control the operation of the process. In this manner, the process controllers may execute and coordinate control routines using the process control devices via the buses and/or other communication links communicatively coupling the process control devices. Large scale process control systems are often configured to perform processes in accordance with batch recipes to produce products. Product designers or engineers prepare recipes during a development phase and store the recipes to be subsequently used a plurality of times by a process control system. A recipe typically includes a combination of unit procedures, operations, and phases, all of which include instructions to control process control devices (e.g., mixers, pumps, transmitters, valves, etc.) to transfer, mix, etc. ingredients in a process control system to generate a product.

Stock cell lines, used in large scale commercial cell culture behave in a predictable manner, and so predefined culture recipes and routines can be used to good effect. That large scale methodology where a predetermined routine is followed is only partially of use in small scale culture, because unique batches of cells derived from different patients rarely behave in the same way so control of their environmental parameters needs to be conducted based on measurement feedback and an iterative approach, rather than wholly or mostly driven by predetermined routines as in large scale culturing. Ideally smaller scale culture is also predictively based i.e. processing measurement data derived from previous parameter measurements, to predict the degree to which certain parameters will change with a step change in inputs, to thereby bring the culture back into an acceptable measured parameter range. That methodology is not problematic until a system failure occurs, then the parameters which are needed for present and future parameter control are lost and the reset or replaced system needs to re-learn what adjustments are needed to maintain the environmental parameters for that, often unique, batch. The default position of a predetermined routine is rarely suited to the unique batch characteristics.

BRIEF SUMMARY

The inventors have realised that there is a need to provide a back-up function in the event of system failure which back-up can accommodate system failure where the failed system was controlling parameters of a cell culture batch. In addition, the inventors have realised that there is need to provide a back-up function where cell batches respond differently to changes in environmental parameters compared to the same changes made to a different batch.

Aspects of the invention are set out in the claims, and thereby, embodiments of the invention provide that where a bioreactor system fails and cannot be restarted, a disposable cell bag which is being used as a culture bioreactor volume can be physically moved to a back-up system and the culture process can be carried on without undue delay, and without having reprogram the back-up system. Various ways to put this procedure into practice are described in more detail below.

Furthermore, advantages and benefits of the present invention will become clearer to the person skilled in the art in view of the detailed description below.

DRAWINGS

The invention will now be described in more detail with reference to the appended drawings, wherein:

FIG. 1b shows operation of a bioreactor system of FIG. 1a;

Figure 2A:
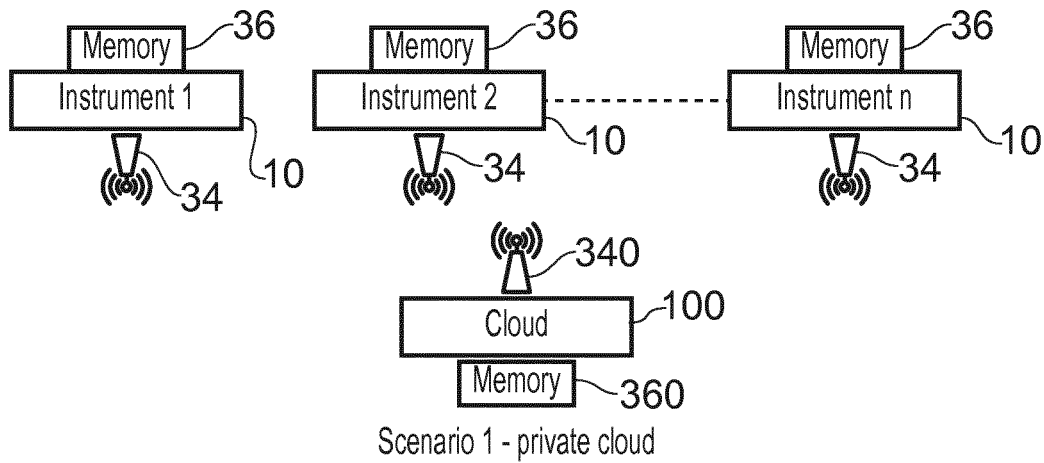
Figure 2B:
Figure 2C:
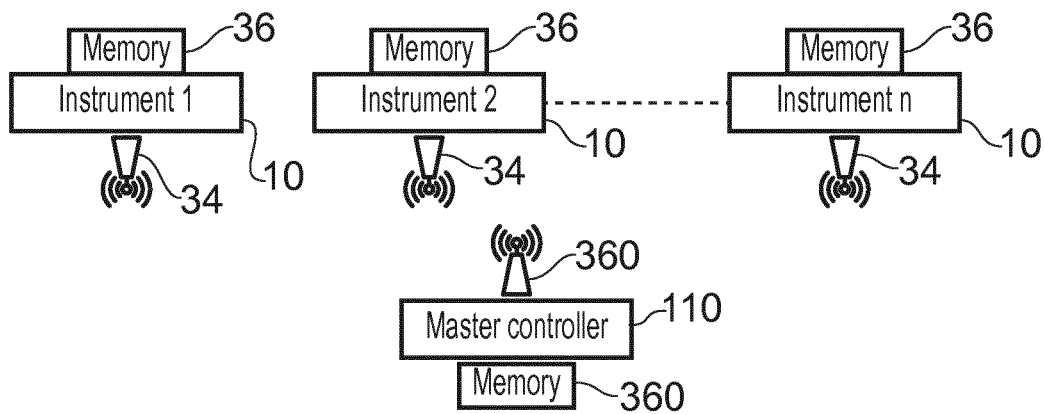
Figure 3:
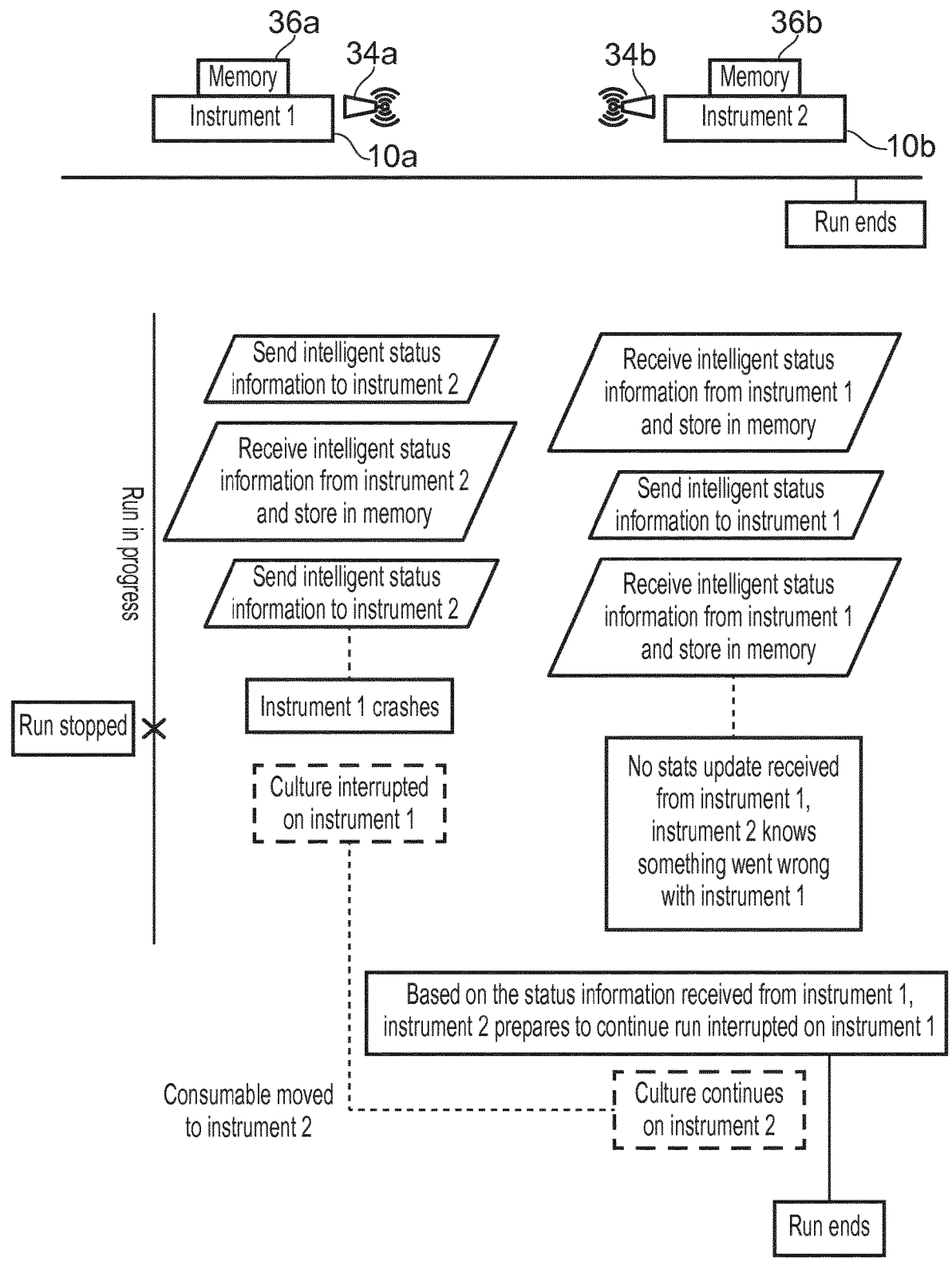

FIGS. 2a 2b and 2c show schematically alternative communication arrangements between plural bioreactor systems; and FIG. 3 shows schematically a system failure recovery routine.

DETAILED DESCRIPTION

Figure 1A:
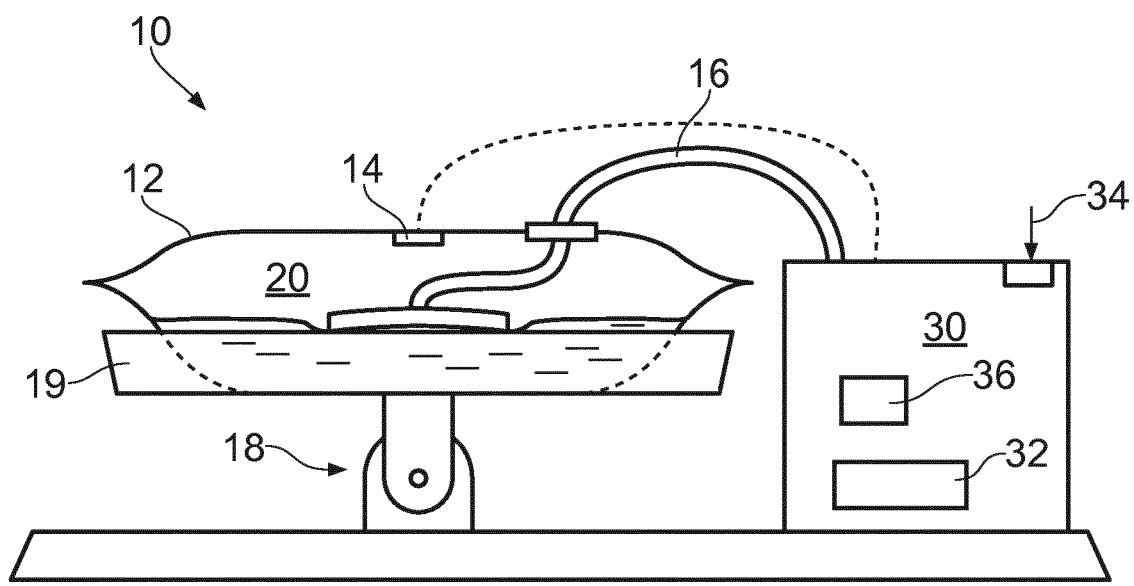
FIG. 1a shows a bioreactor system.

FIG. 1a shows a bioreactor system 10, which is, mostly commercially available, for example as sold under the trade name Xuri Cell Expansion System. The system includes a flexible bioreactor cell bag 12 which defines a cell culture volume 20. The volume 20 includes cell culture liquid medium and a gas head space, all providing an artificial environment in which the cells are cultured. The cell bag is rocked on a heated rocking platform 18, including a support tray 19 to warm, mix and oxygenate the liquid medium. Idealised culture conditions vary for each cell type, but the medium supplies the essential nutrients (amino acids, carbohydrates, vitamins, minerals), growth factors, hormones, and gases (O2, CO2), and regulates the physicochemical environment. The environment is monitored for example by one or more monitor or sensors 14, shown schematically, and appropriate changes to the environment (for example supply of fresh medium or gases, or the removal of liquids or gases), can be made via conduit 16. A process controller 30, shown here alongside the platform, is used to control the environment according to predetermined program steps which are modified by the values received from the monitor(s) or sensor(s) 14, by means of process control devices 32 i.e. fluid pumps, heating elements and their controllers, motors and their speed controllers for the rocking tray 18, and gas control valves. Whilst it is possible to automatically monitor the cell density of the medium using a monitor that is incorporated into the monitor 14, it is also possible to manually remove a sample of medium and either physically count the number of cells in a representative sample under a microscope, or to have the cells in the sample remotely counted for example using a commercially available cell counter. In that instance the program run by the controller 30 can be updated with the cell density, which is one of the important feedback values needed to monitor the progression of cell culture.

An improvement over known bioreactor systems is the inclusion of a communication device 34 which enables the bioreactor system to read or write data from or to another system, for example another bioreactor system, or another data processor which has a remote memory or is connected to a memory. In the present embodiment, the communication device is a wireless link for example employing an IEEE 802 standard such as: a wireless local area network (WLAN) or device as defined by IEEE 802.11 standards, such as a WiFi product; or a wireless personal area network (WPAN) protocol as defined in IEEE 802.15.4 e.g. Zigbee products; or a IEEE 802.15.1 standard such as Bluetooth products. Another improvement is a memory 36 which keeps data and is accessible by, and transferable to other similar systems or remote memories, and operatively described in more detail below. In addition, the predetermined program steps which are run by the controller 30 can be modified by feedback from the measurement devices 14 to update the memory with data relating any modifications necessary to maintain the pre-set parameters of the culture process.

The memory 36 is any generally non-volatile data store which is preferably electrically rewriteable such as a USB connected memory, flash memory, a hard disk, or remote cloud memory. NAND or NOR type flash memory is preferred because it can be rewritten in a scrolling manner as the cell culture process progresses, and in the event of a sudden failure, the memory is frozen. Where a remote memory is used, the physical location does not matter, and communication with that remote memory can be via the wireless communication device 34, although local memory is preferred because it the memory needed to be completely reliable.

Figure 1B:
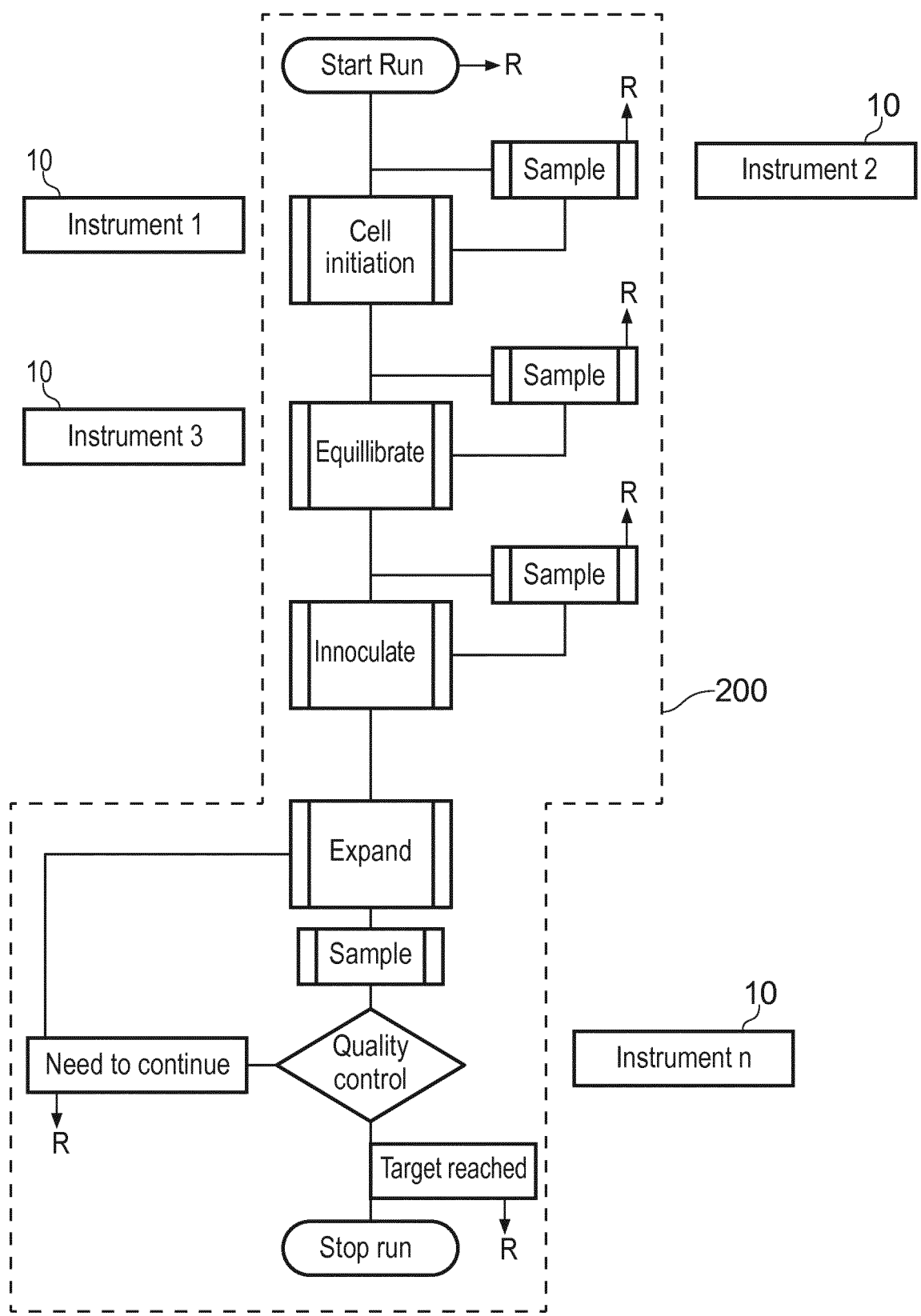

FIG. 1b shows a typical cell culture process 200, where isolated cells are initiated into the volume 20 for example they are injected into the volume along with a small quantity of culture medium through an inlet in the cell bag 12. Equilibration, inoculation, and expansion then follow. Each stage of the cell culture process is monitored, typically for head space gas content, with the aim of maintain $O_2$ and $CO_2$ levels by means of gas inputs, culture medium content with the aim of maintaining pH levels by means of liquid inputs and regular cell samples are taken, which monitor cell density and cell viability numbers. This information is used to modify the cell culture process, for example by adding more oxygen where those levels are low or increase the concentration of growth factor where the cell count has not increased as expected. In an improvement to known cell culture process steps, the completion of each stage, or the completion of each iteration in a stage of the cell culture process is recorded (step R) in the memory 36 along with data representing a log of the associated monitored values and the inputs made. In this way not just the cell culture progression is recorded but the underlying inputs used at each stage are recorded, so they can be replicated without having to repeat iterations of inputs to learn the effects of the inputs on a cell batch.

FIGS. 2a, 2b and 2c show schematically examples of possible system communications. In FIG. 2a plural systems 10 are used, each having a communication device 34 of the type described above and two way communication with a private (pseudo) cloud storage, in the form of a dedicated communication server 100 having a server communication device 340 and a non-volatile memory 360 which is used to store cell culture progress data uploaded from each of the plural systems 10 in substantially real time, using the communication devices 34 and 340, operated for example according to any one of the wireless protocols mentioned above. The two way communication enables one of the systems 10 to interrogate the memory 360 and download data representative of the progress of the culture process from any one of the other sister systems, for example when that other system fails. The new system can then quickly carry on the cell culture process from the point where the failed system stopped the process, once the cell bag 12, or other bioreactor is moved to the new system.

FIG. 2b shows a more simple arrangement, where each system 10 in a family communicates directly with all other sister systems. In this arrangement, the memories 36 have pages relating to each family member and which are updated in real time with data relating to their sister systems. In that way one system can take over the culture processing as described above should there be a failure of another system. Also, since multiple copies of every system's progress is recorded, catastrophic failure where multiple systems fail, for example in the event of a lightning strike, can be recoverable, because only one system's memory needs to survive.

FIG. 2c shows another communication arrangement employing, an active master controller 110 which communicates with a family of systems 10. The master controller functions in a similar manner to the server 100, except that progression data can be scrutinised for example to monitor trends, and the master controller can communicate with other devices should a data trend show a possible imminent failure or should a monitored value drift toward the limit of a range.

FIG. 3 shows a system failure recovery routine. Whilst the routine is based on the system arrangement shown in FIG. 2b, it is equally applicable to other arrangements, for example as shown in FIG. 2a or 2c. In the routine shown, the system 10a (in the figure referred to as 'instrument 1') is being controlled to progress through a cell culture process according to FIG. 1b. During this time its progress is recorded in its memory 36aand that progress is also communicated externally of the system 10a via the communication device 34a, and is received at least by the communication device 34b, and further recorded by another system, in this case a system 10b (in the figure referred to as 'instrument 2') in real time into the memory 36b, even though the system 10b is occupied with cell culture. Once the system 10b has finished it's cell culture process (run ends), it becomes available for further processing. In the alternative the system 10b can be kept unoccupied as a reserve system in case of failure of another system. In any case, the system 10b has a memory page which includes data representing the progress of the system 10a and any other system in the family. In this example, system 10a has failed part way through its culture process, and system 10b is alerted to the failure because it no longer is receiving any updates for the system 10a. Manual transfer of the cell bag 12 is needed in this example from system 10a to system 10b, some reconnection of the inputs and monitors will be required, and then system 10b can carry on with the cell culture process from the point where system 10a failed. Whilst the cell bag transfer step is expected to be manual, it is entirely possible that that step can be made automatic for example by employing conventional robotic manipulators which are pre-programmed to undertake the desired transfer movements and manipulations. In the case where robots are employed, it would be more desirable to transfer the cell bag with the heated tray 17. The next step is to instruct system 10b to start cell culture processing so as to complete the remaining steps of the incomplete process previously run on system 10a.

It will be noted that, in the above example bioreactor 10a (instrument 1) operates (at least until its failure) in a similar manner to the bioreactor system 10b, in that the memory 10a is used to store data relating to the progress of adjacent bioreactor systems, should it be needed to complete cell culture processing of a failed system. In a larger group of systems, say 3 or more systems working together, each system will be monitoring all other systems, or has access to memory where all the systems' progress is recorded, so the system which next finishes its cell processing can be selected to finish a failed system's processing. Thereby, it is not necessary to have a system unoccupied and waiting as a back-up if the sequence of the cell culture processes is staggered across multiple systems, and the time between failure and recommencement of the culture process is then only a few hours.

Thus the embodiments above provide a reliable failure or error recovery of potentially irreplaceable cells, and where failure/errors occur, the recovery data stored in memory can be used to bring the environment of the cell batch quickly into conformity with parameter ranges.

The invention is not to be seen as limited by the embodiments described above, but can be varied within the scope of the appended claims as is readily apparent to the person skilled in the art. For example, while it is convenient to have wireless communication of culture progress, a communication bus operable with input/output devices would work equally well as a communication device, for local communications. Use of removable solid state memory is another alternative, and eliminates the need for a communication device 34. In operation, the solid state memory can be removed from a failed system and inserted into a vacant system to provide the data needed to determine which process steps need to be completed.

The invention claimed is:

1. Apparatus comprising a first cell culture bioreactor system for culturing cells to a predetermined cell density or quantity, the system including a bioreactor volume, a first process controller, process control devices which provide inputs for the bioreactor volume and culture parameter measurement devices, wherein the first process controller is operable according to plural control program steps to control the process control devices to provide inputs for a suitable cell culture environment in the bioreactor volume, and is further operable according to control program steps modified by feedback values from the culture parameter measurement devices, and comprises a first memory operable to record data indicative of the progress of the control program steps, the apparatus further including a communication device operable to communicate externally of that system the contents of the first memory to a shared memory accessible by one or more additional bioreactor system, and the apparatus further comprising the one or more additional bioreactor systems, and wherein the data from the first memory of the first bioreactor system is made available to the shared memory via the communication device, further wherein a second process controller of one a second cell culture bioreactor system of the additional bioreactor systems is configured, in response to a failure of the first bioreactor system, to access the shared memory to obtain with data necessary to determine which program steps run on the first process controller of the first bioreactor system are incomplete, and to determine which program steps need to be completed in a process to obtain the predetermined cell density or quantity from the volume, and to resume the culturing of the cells to the predetermined cell density or quantity on the second cell culture bioreactor system.

2. The apparatus as claimed in claim 1, wherein the first memory is further operable to record data indicative of the feedback values of parameters measured by respective parameter measurement devices at respective program steps.

3. The apparatus as claimed in claim 1, wherein the data provided to the second process controller indicates which, if any, complete steps have been modified by the feedback values from the measurement devices of the first bioreactor system and optionally which, if any, incomplete steps require modification based on previously recorded data indicative of the feedback values.

4. The apparatus as claimed in claim 1, wherein each bioreactor system includes a bioreactor in the form of a flexible cell bag, separable from the remainder of the system so as to be transferrable between bioreactor systems.

5. The apparatus as claimed in claim 4, wherein each bioreactor system includes a heated rocking tray for supporting the cell bag and the tray is separable from the remainder of the system so as to be transferrable between bioreactor systems along with the cell bag.

6. The apparatus as claimed in claim 1, further comprising a communication server, the communication server comprising the shared memory and in communication with the first bioreactor system and the one or more additional bioreactor system.

7. The apparatus as claimed in claim 1, wherein the first bioreactor system lacks direct communications with the one or more additional bioreactor system.

8. The apparatus as claimed in claim 1, wherein the second cell culture bioreactor system comprises the shared memory.

9. A method for culturing cells in a bioreactor, the method comprising the steps of:
   a) providing a first cell culture bioreactor system, including a bioreactor volume, process controller, process control devices and culture parameter measurement devices, and;
   b) operating the process controller and process devices to provide a suitable cell culture environment according to plural program steps and, at least partially in response to culture parameters measured by said measurement devices;
   c) recording in a shared memory accessible to one or more additional bioreactor systems which steps are complete or incomplete, and measured parameters corresponding to at least one of the steps in a culture process to obtain a predetermined cell density or quantity from the volume; and
   d) rectifying a failure in the first cell culture bioreactor system by at least communicating data from the shared memory to a respective process controller of one of the one or more additional bioreactor systems with data necessary to determine which program steps run on the controller of the first bioreactor system are incomplete in the culture process and resuming progress of the culture process using the one of the additional bioreactor systems.

10. The method as claimed in claim 9, including in step d) the steps of: communicating, from a communication server comprising the shared memory, data from the shared memory, to provide the respective process controller of one of the additional bioreactor systems with data necessary to determine which, if any, complete steps have been modified by feedback values from the measurement devices of the first bioreactor system and/or which, if any, incomplete steps require modification based on previously recorded data indicative of the feedback values.

11. The method for culturing cells in a bioreactor as claimed in claim 9, further including a later step of transferring the bioreactor volume from the first bioreactor system to one of the additional bioreactor systems and completing any incomplete programs steps.

12. The method according to claim 9, wherein the first and additional bioreactor systems operate cell culture processes according to the program steps, and following a failure of another system, the first to obtain a predetermined cell density or quantity in its respective volume is selected as the system to finish any incomplete cell culture process of the failed system.

* * * * *